(12) United States Patent
Grainger et al.

(10) Patent No.: US 8,076,323 B2
(45) Date of Patent: *Dec. 13, 2011

(54) ANTI-INFLAMMATORY AGENTS

(75) Inventors: David J. Grainger, Cambridge (GB); David John Fox, Coventry (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/877,041

(22) Filed: Sep. 7, 2010

(65) Prior Publication Data

US 2011/0003792 A1    Jan. 6, 2011

Related U.S. Application Data

(63) Continuation of application No. 11/922,277, filed as application No. PCT/GB2006/002217 on Jun. 14, 2006, now Pat. No. 7,803,794.

(30) Foreign Application Priority Data

| Jun. 15, 2005 | (GB) | .................................. | 0512241.1 |
| Aug. 10, 2005 | (GB) | .................................. | 0516468.6 |

(51) Int. Cl.
  *A61K 31/55* (2006.01)
  *A61K 31/455* (2006.01)
  *A61K 31/40* (2006.01)

(52) U.S. Cl. ..................... 514/212.03; 514/315; 514/424

(58) Field of Classification Search ............. 514/212.03, 514/315, 424
  See application file for complete search history.

(56) References Cited

U.S. PATENT DOCUMENTS 7,803,794 B2 * 9/2010 Grainger et al. ......... 514/212.03

FOREIGN PATENT DOCUMENTS

| EP | 0351856 A2 | 1/1990 |
| GB | 2418425 B2 | 9/2008 |
| WO | 98/28300 A1 | 7/1998 |
| WO | 03/057200 A2 | 7/2003 |
| WO | 2006/016152 A1 | 2/2006 |
| WO | 2006/134384 A1 | 12/2006 |
| WO | 2006/134385 A1 | 12/2006 |

OTHER PUBLICATIONS

International Preliminary Report on Patentability received for PCT Patent Application No. PCT/GB2006/002217, mailed on Jan. 3, 2008, 7 pages.
International Search Report and Written Opinion received for PCT Patent Application No. PCT/GB2006/002217, mailed on Oct. 19, 2006, 1 pages.
Search Report received for United Kingdom Patent Application No. GB0512241.1 UK mailed on Sep. 9, 2005, 1 page.
Search Report received for United Kingdom Patent Application No. GB0516468.6 UK mailed on Jan. 25, 2007, 1 page.
Fox, David J., et al., "Identification of 3-(Acylamino)azepan-2-ones as as Stable Broad-Spectrum Chemokine Inhibitors Resistant to Metabolism in Vivo", J. Med. Chem 48, (2005), pp. 867-874.

* cited by examiner

*Primary Examiner* — Raymond Henley, III
(74) *Attorney, Agent, or Firm* — VLP Law Group LLP; Richard G. A. Bone

(57) ABSTRACT

The invention provides compounds, pharmaceutical compositions and uses of compounds and salts thereof of general formula (I), for the preparation of a medicament for treatment of an inflammatory disorder, (I)

Figure 1:
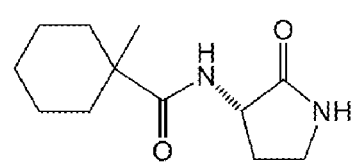
Figure 1:
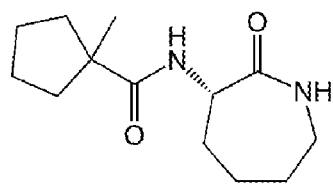
Figure 1:
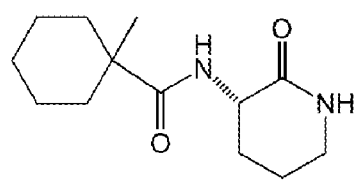
Figure 1:
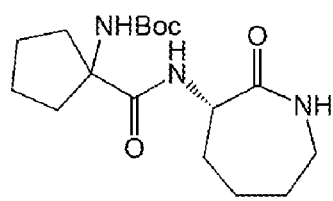
Figure 1:
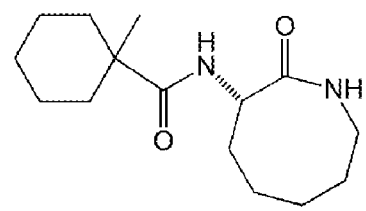
Figure 1:
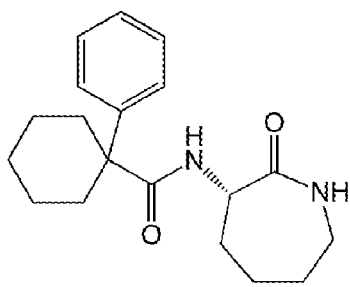
Figure 1:
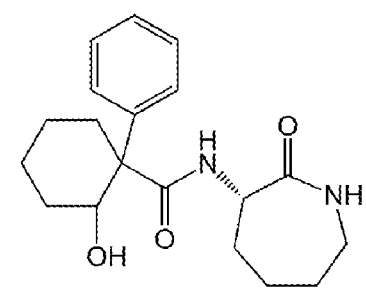
Figure 1:
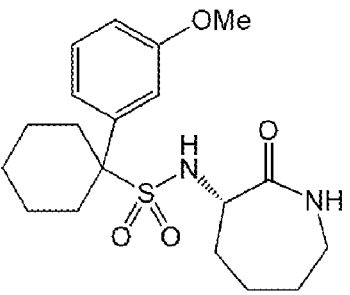
Figure 1:
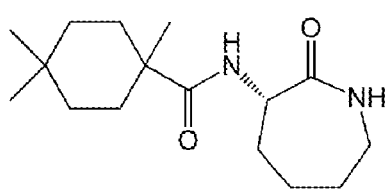
Figure 1:
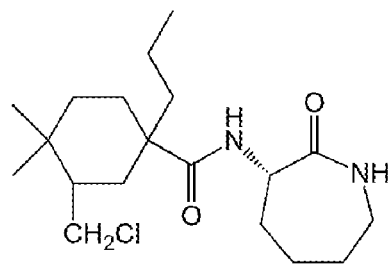

but excluding (S)-3-(1'-methylcyclohexylcarbonylamino)-caprolactam: wherein
z is 1, 2, 3 or 4;
A is —CO— or —SO$_2$—;
Q is linear or branched alkyl, alkenyl, alkynyl, alkoxy, oxyalkyl, aminoalkyl, alkylamino, alklylaminoalkyl, haloalkyl, aryl or substituted aryl;
T$^1$ and T$^2$ together constitute a cycloalkyl, cycloalkenyl or polycycloalkyl radical composed of n additional carbon atoms, where n is between 2 and 7;
and each hydrogen atom bonded to the carbon atoms in the ring generated by T$^1$ and T$^2$ may be independently be substituted by a group R$^1$, where R$^1$ is independently selected from an alkyl, haloalkyl, alkoxy, haloalkoxy, alkenyl, alkynyl or alkylamino radical of 1 to 20 carbon atoms;
or each R$^1$ is independently selected from fluoro, chloro, bromo, iodo, hydroxy, oxyalkyl, amino, aminoalkyl or aminodialkyl radical.

49 Claims, 1 Drawing Sheet

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial
<220> FEATURE:
<223> OTHER INFORMATION: Synthetic human protein analogue
<300> PUBLICATION INFORMATION:
<301> AUTHORS: Reckless et al.
<302> TITLE: Identification of oligopeptide sequences which inhibit
      migration induced by a wide range of chemokines
<303> JOURNAL: Biochemical Journal
<304> VOLUME: 340
<306> PAGES: 803-811
<307> DATE: 1999

<400> SEQUENCE: 1

Cys Gln Ile Trp Lys Gln Lys Pro Asp Leu Cys
1               5                   10
```

ANTI-INFLAMMATORY AGENTS

This application claims the benefit of priority under 35 U.S.C. §120 to, and is a continuation of U.S. patent application Ser. No. 11/922,277, filed Jan. 9, 2009, now U.S. Pat. No. 7,803,794, which application is the U.S. national stage under 35 U.S.C. §371 of International Application Number PCT/GB2006/02217, having an international filing date of Jun. 14, 2006, which claims benefit of priority to United Kingdom Patent Application Number 0512241.1, filed Jun. 15, 2005, and United Kingdom Patent Application Number 0516468.6, filed Aug. 10, 2005, all of which applications are incorporated herein by reference in their entireties.

The invention relates to the use of 1'-substituted cyclohexyl derivatives of 3-aminolactams for preparing a medicament intended to prevent or treat inflammatory disorders.

Inflammation is an important component of physiological host defense. Increasingly, however, it is clear that temporally or spatially inappropriate inflammatory responses play a part in a wide range of diseases, including those with an obvious leukocyte component (such as autoimmune diseases, asthma or atherosclerosis) but also in diseases that have not traditionally been considered to involve leukocytes (such as osteoporosis or Alzheimer's disease).

The chemokines are a large family of signalling molecules with homology to interleukin-8 which have been implicated in regulating leukocyte trafficking both in physiological and pathological conditions. With more than fifty ligands and twenty receptors involved in chemokine signalling, the system has the requisite information density to address leukocytes through the complex immune regulatory processes from the bone marrow, to the periphery, then back through secondary lymphoid organs. However, this complexity of the chemokine system has at first hindered pharmacological approaches to modulating inflammatory responses through chemokine receptor blockade. It has proved difficult to determine which chemokine receptor(s) should be inhibited to produce therapeutic benefit in a given inflammatory disease.

More recently, a family of agents which block signalling by a wide range of chemokines simultaneously has been described: Reckless et al., Biochem J. (1999) 340:803-811. The first such agent, a peptide termed "Peptide 3", was found to inhibit leukocyte migration induced by 5 different chemokines, while leaving migration in response to other chemoattractants (such as fMLP or TGF-beta) unaltered. This peptide, and its analogs such as NR58-3.14.3 (i.e. Sequence ID No. 1 c(DCys-DGin-DIle-DTrp-DLys-DGln-DLys-DPro-DAsp-DLeu-DCys)-NH$_2$), are collectively termed "Broad Spectrum Chemokine Inhibitors" (BSCIs). Grainger et al., Biochem. Pharm. 65 (2003) 1027-1034 have subsequently shown BSCIs to have potentially useful anti-inflammatory activity in a range of animal models of diseases. Interestingly, simultaneous blockade of multiple chemokines is not apparently associated with acute or chronic toxicity, suggesting this approach may be a useful strategy for developing new anti-inflammatory medications with similar benefits to steroids but with reduced side-effects.

However, peptides and peptoid derivatives such as NR58-3.14.3, may not be optimal for use in vivo. They are quite expensive to synthesise and have relatively unfavourable pharmacokinetic and pharmacodynamic properties. For example, NR58-3.14.3 is not orally bioavailable and is cleared from blood plasma with a half-life period of less than 30 minutes after intravenous injection.

Two parallel strategies have been adopted to identify novel preparations which retain the anti-inflammatory properties of peptide 3 and NR58-3.14.3, but have improved characteristics for use as pharmaceuticals. Firstly, a series of peptide analogs have been developed, some of which have longer plasma half-lives than NR58-3.14.3 and which are considerably cheaper to synthesise. Secondly, a detailed structure:activity analysis of the peptides has been carried out to identify the key pharmacophores and design small non-peptidic structures which retain the beneficial properties of the original peptide.

This second approach yielded several structurally distinct series of compounds which retained the anti-inflammatory properties of the peptides, including 16-amino and 16-aminoalkyl derivatives of the alkaloid yohimbine, as well as a range of N-substituted 3-aminoglutarimides. (Reference: Fox et al., J Med Chem 45 (2002) 360-370: WO 99/12968 and WO 00/42071.) All of these compounds are broad-spectrum chemokine inhibitors which retain selectivity over non-chemokine chemoattractants, and a number of them have been shown to block acute inflammation in vivo.

The most potent and selective of these compounds was (S)-3-(undec-10-enoyl)-aminoglutarimide (NR58.4), which inhibited chemokine-induced migration in vitro with an $ED_{50}$ of 5 nM. However, further studies revealed that the aminoglutarimide ring was susceptible to enzymatic ring opening in serum. Consequently, for some applications (for example, where the inflammation under treatment is chronic, such as in autoimmune diseases) these compounds may not have optimal properties, and a more stable compound with similar anti-inflammatory properties may be superior.

As an approach to identifying such stable anlogs, various derivatives of (S)-3-(undec-10-enoyl)-aminoglutarimide have been tested for their stability in serum. One such derivative, the 6-deoxo analog (S)-3-(undec-10-enoyl)-tetrahydro-pyridin-2-one, is completely stable in human serum for at least 7 days at 37° C., but has considerably reduced potency compared with the parental molecule.

One such family of stable, broad spectrum chemokine inhibitors (BSCIs) are the 3-amino caprolactams, with a seven-membered monolactam ring. However, further useful anti-inflammatory compounds may be generated from other 3-aminolactams with different ring size.

One particularly useful example of such a compound is (S)-3-(1'-adamantanecarbonylamino)caprolactam. This compound is a potent inhibitor of leukcoyte recruitment in vitro, and has powerful anti-inflammatory activity in vivo (comparable to the steroid preparation dexamethasone), whether delivered by an oral route, or by injection. (S)-3-(1'-adamantanecarbonylamino)caprolactam is crystalline, relatively straightforward and inexpensive to prepare and has good pharmaceutical properties. However, the adamantine ring is does not facilitate substitutions of the ring hydrogen atoms, and limits the scope for exploring further derivatives for novel or improved properties.

(S)-3-(1'-methylcyclohexylcarbonylamino)-caprolactam (GB 0417863.8) retains the key 2',2' disubstituted tetrahedral carbon atom, and hence many of the beneficial properties, of (S)-3-(1'-adamantanecarbonylamino)caprolactam, but is amenable to extensive substitution, providing a wealth of new derivatives which can be screened for novel or improved properties. Examples include compounds where the cyclohexyl ring is exchanged for rings of different sizes (from cyclopropyl to cyclo-ocytl), compounds where the methyl substituent at the 1' position is exchanged for other substituents (including heteroatoms), compounds where the ring itself is substituted at various positions and compounds where several of these modifications are made simultaneously.

The invention provides the use of a compound of general formula (I), or a pharmaceutically acceptable salt thereof, for the preparation of a medicament intended to treat inflammatory disorder:

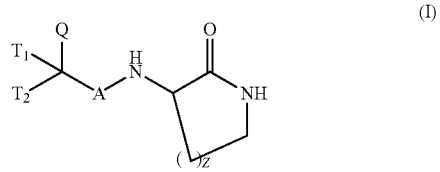
(I)

but excluding (S)-3-(1'-methylcyclohexylcarbonylamino)-caprolactam: wherein
z is 1, 2, 3 or 4;
A is —CO— or —SO$_2$—;
Q is linear or branched alkyl, alkenyl, alkynyl, alkoxy, oxyalkyl, aminoalkyl, alkylamino, alklylaminoalkyl, haloalkyl, aryl or substituted aryl, or tert-Butoxycarbonylamino;
T$^1$ and T$^2$ together constitute a cycloalkyl, cycloalkenyl or polycycloalkyl radical composed of n additional carbon atoms, where n is between 2 and 7;
and each hydrogen atom bonded to the carbon atoms in the ring generated by T$^1$ and T$^2$ may be independently be substituted by a group R$^1$, where R$^1$ is independently selected from an alkyl, haloalkyl, alkoxy, haloalkoxy, alkenyl, alkynyl or alkylamino radical of 1 to 20 carbon atoms;
or each R$^1$ is independently selected from fluoro, chloro, bromo, iodo, hydroxy, oxyalkyl, amino, aminoalkyl or aminodialkyl radical.

The carbon atom at position 3 of the lactam ring is asymmetric and consequently, the compounds according to the present invention have at least two possible enantiomeric forms, that is, the "R" and "S" configurations. The present invention encompasses the two enantiomeric forms and all combinations of these forms, including the racemic "RS" mixtures. With a view to simplicity, when no specific configuration is shown in the structural formulae, it should be understood that the two enantiomeric forms and their mixtures are represented.

Many of the compounds according to the present invention will have one or more additional stereocentres, and may therefore exist in very many enantiomeric or diastereomeric configurations. The present invention encompasses all these enantiomeric and diastereomeric forms, as well as all combinations of these forms, including racemic mixtures. With a view to simplicity, where no specific configuration is shown at a given position in a structural formula, it should be understood that all possible enantiomeric or diastereomeric forms, and their mixtures, are represented.

Preferably, the compounds of general formula (I) or pharmaceutically acceptable salts thereof used according to this aspect of the invention will be compounds of general formula (I')

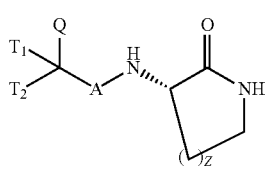
(I')

wherein A, Q, T$^1$, T$^2$ and z have the same meanings as above.
Preferably, the compounds of general formula (I) or (I'), or their pharmaceutically acceptable salts, will be such that the ring or rings composed by T$^1$ and T$^2$ together constrain the bond angles at the alpha-carbon to be essentially tetrahedral (i.e. sp3 hybrid bonds). The "alpha carbon" is either at the 2-position (relative to the amide carbonyl) or at the 1-position (relative to the sulfonamide sulfonyl group).

Any substituent R$^1$ may be a substituent at any permissible position on the ring or rings of the cyclo-group composed by T$^1$ and T$^2$. In particular it is to be noted that all the compounds of the invention have an "alpha carbon" which is both part of the cyclo group and is itself substituted. The definition encompasses compounds of the invention with no substitution (i.e. all R$^1$=hydrogen), compounds of the invention with mono substitution (i.e. one R$^1$ which is not hydrogen), and also multiple substitution (i.e. at least two R$^1$ groups are not hydrogen).

The invention also provides pharmaceutical compositions comprising, as active ingredient, a compound of general formula (I), or a pharmaceutically acceptable salt thereof, and at least one pharmaceutically acceptable excipient and/or carrier:

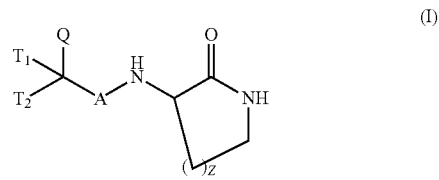
(I)

but excluding (S)-3-(1'-methylcyclohexylcarbonylamino)-caprolactam: wherein
z is 1, 2, 3 or 4;
A is —CO— or —SO$_2$—;
Q is linear or branched alkyl, alkenyl, alkynyl, alkoxy, oxyalkyl, aminoalkyl, alkylamino, alklylaminoalkyl, haloalkyl, aryl or substituted aryl, or tert-Butoxycarbonylamino;
T$^1$ and T$^2$ together constitute a cycloalkyl, cycloalkenyl or polycycloalkyl radical composed of n additional carbon atoms, where n is between 2 and 7;
and each hydrogen atom bonded to the carbon atoms in the ring generated by T$^1$ and T$^2$ may be independently be substituted by a group where R$^1$ is independently selected from an alkyl, haloalkyl, alkoxy, haloalkoxy, alkenyl, alkynyl or alkylamino radical of 1 to 20 carbon atoms;
or each R$^1$ is independently selected from fluoro, chloro, bromo, iodo, hydroxy, oxyalkyl, amino, aminoalkyl or aminodialkyl radical.

Preferably, the compounds of general formula (I) or pharmaceutically acceptable salts thereof used according to this aspect of the invention will be compounds of general formula (I')

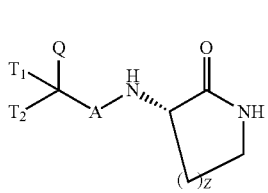
(I')

wherein A, Q, T$^1$, T$^2$ and z have the same meanings as above.
By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax. Other appropriate pharmaceutically acceptable excipients and/or carriers will be known to those skilled in the art.

The pharmaceutical compositions according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The invention also provides compounds and salts thereof of general formula (I)

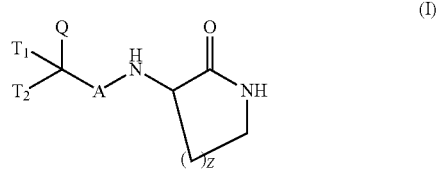

but excluding (S)-3-(1'-methylcyclohexylcarbonylamino)-caprolactam: wherein
z is 1, 2, 3 or 4;
A is —CO— or —SO$_2$—;
Q is linear or branched alkyl, alkenyl, alkynyl, alkoxy, oxyalkyl, aminoalkyl, alkylamino, alkylaminoalkyl, haloalkyl, aryl or substituted aryl, or tert-Butoxycarbonylamino;
$T^1$ and $T^2$ together constitute a cycloalkyl, cycloalkenyl or polycycloalkyl radical composed of n additional carbon atoms, where n is between 2 and 7;
and each hydrogen atom bonded to the carbon atoms in the ring generated by $T^1$ and $T^2$ may be independently be substituted by a group $R^1$, where $R^1$ is independently selected from an alkyl, haloalkyl, alkoxy, haloalkoxy, alkenyl, alkynyl or alkylamino radical of 1 to 20 carbon atoms;
or each $R^1$ is independently selected from fluoro, chloro, bromo, iodo, hydroxy, oxyalkyl, amino, aminoalkyl or aminodialkyl radical.

Preferably, the compounds of general formula (I) or salts thereof used according to this aspect of the invention will be compounds of general formula (I')

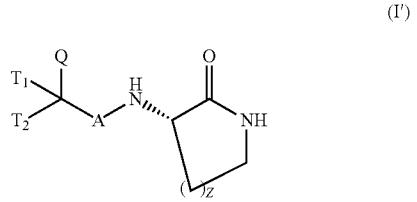

wherein A, Q, $T^1$, $T^2$ and z have the same meanings as above.

Preferably, the compounds of general formula (I) or (I') when used in the invention, or their salts, will be such that the ring or rings composed of $T^1$ and $T^2$ constrain the bond angles at the alpha-carbon to be essentially tetrahedral (i.e. sp3 hybrid bonds).

Comparison of several compound series (for example, where $T^1$ and $T^2$ together specify a cyclohexyl radical, where Q=methyl and where A=—CO—) demonstrates that compounds of formula (I) or (I') have useful activity irrespective of the size of the lactam ring (z is 1, 2, 3 or 4).

Comparison of compounds within a series where $T^1$ and $T^2$ together specify a cyclohexyl radical and where A=—CO— demonstrate that compounds with different substitutions at Q are active according to the invention. For example, in this series where Q=phenyl or methyl the compounds have activity according to the invention, both for the sub-series where z=2 and where z=3. In the same way, compounds where Q is not alkyl or aryl (for example when Q=NHCOOtBu) have also been shown to have activity according to the invention.

Similarly, compounds where $T^1$ and $T^2$ together specify a ring other than cyclohexyl have been shown to have activity according to the invention (for example, where $T^1$ and $T^2$ together specify a cyclopentyl radical).

Comparison of compounds in which the ring specified by $T^1$ and $T^2$ has various substituents with analogous compounds in which the ring specified by $T^1$ and $T^2$ is unsubstituted demonstrates that compounds with substituted rings specified by $T^1$ and $T^2$ are active according to the invention (for example, where $T^1$ and $T^2$ together specify a cyclohexyl radical, Q is methyl, A=—CO— and z=3, the compound is active according to the invention whether or not the $R^1$ group at the 4 position of the cyclohexyl ring is substituted with a tert-butyl group; alternatively where $T^1$ and $T^2$ together specify a cyclohexyl radical, Q is methyl, A=—CO— and z=3, the compound is active according to the invention whether or not the $R^1$ group at the 2 position of the cyclohexyl ring is substituted with a hydroxyl group)

In particular, preferred compounds of general formula (I) or (I') and their salts according to any aspect of the present invention are selected from the group consisting of:
—(S)-3-(2'-hydroxy-1'-methylcyclohexanecarbonyl)amino-caprolactam;
—(S)-3-(1'-Phenylcyclohexanecarbonyl)amino-caprolactam;
—(S)-3-(1'-Phenylcyclohexanecarbonyl)amino-tetrahydropyridin-2-one;
—(S)-3-(cis-4'-tert-Butyl-1'-methyl-1'-cyclohexanecarbonyl)amino-caprolactam;
—(S)-3-(1'-Methylcyclohexanecarbonyl)amino-tetrahydropyridin-2-one;
—(S)-3-(1'-Methylcyclohexanecarbonyl)amino-pyrrolidin-2-one;
—(S)-3-(1'-((tert-Butoxycarbonylamino)cyclopentanecarbonyl)amino-caprolactam;
—(S)-3-(3'-hydroxy-1'-adamantanecarbonyl)amino-caprolactam
and the salts thereof.

The invention also provides the sulfonamide analogues of the exemplified compounds (where A=—SO$_2$—): i.e. the sulfonyl-amino-lactam equivalents of the said compounds.

The invention includes compounds, compositions and uses thereof as defined, wherein the compound is in hydrated or solvated form.

The amide derivatives of 3-amino lactams described here are functional BSCIs. They are relatively inexpensive to synthesise, using facile synthesis routes provided herein; they are stable in human serum and consequently have excellent pharmacokinetic properties; they are orally bioavailable; they are highly potent broad-spectrum chemokine inhibitors in vitro with excellent selectivity over non-chemokine chemoattractants; they are highly potent and effective anti-inflammatory agents in vivo in rodent models of inflammation; their administration is not associated with any significant acute toxicity at the doses necessary to achieve a maximal therapeutic effect. Taken together, these properties suggest that amide derivatives of 3-aminolactams represent anti-inflammatory medications with advantages over previously described compounds.

In comparison to the prior art the improvement of the present invention lies in the provision of the 3-amino lactam moiety with a side chain having one or more alkyl/alkenyl rings to constrain the bond angles at the alpha carbon of the side chain. Compounds of this invention are significantly superior to compounds with linear alleyl chains (whether alkyl amides or alkyl sulfonamides). In addition, we show that a 1'-substituted (that is, Q is not hydrogen) ring system is optimal for constraining the bond angles at the alpha carbon of the sidechain, and that such compounds are suitable for diverse substitution in order to generate compounds to be tested for novel or improved activities.

Prior art peptides (such as NR58-3.14.3) have the disadvantages that: (a) they are expensive and require solid phase synthesis (at least for the longer ones) and (b) they clear very quickly via the kidneys and (c) they are generally less potent.

The prior art aminoglutarimides are cheap, not cleared quickly via the kidneys and more potent BUT they do not show metabolic stability.

The improvement described here, the aminolactams, are cheap, not cleared by the kidney and even more potent, and are also metabolically stable. The compounds of the present invention are amenable to diverse and facile substitution to generate a broad range of compounds with anti-inflammatory activity which can be tested for novel or improved activities in various assays both in vitro and in vivo.

According to this invention, inflammatory disorders intended to be prevented or treated by the compounds of general formula (I) or (I') or the pharmaceutically acceptable salts thereof or pharmaceutical compositions or medicaments containing them as active ingredients include notably:

autoimmune diseases, for example such as multiple sclerosis;

vascular disorders including stroke, coronary artery diseases, myocardial infarction, unstable angina pectoris, atherosclerosis or vasculitis, e.g., Behçet's syndrome, giant cell arteritis, polymyalgia rheumatica, Wegener's granulomatosis, Churg-Strauss syndrome vasculitis, Henoch-Schönlein purpura and Kawasaki disease;

viral infection or replication, e.g. infections due to or replication of viruses including pox virus, herpes virus (e.g., Herpesvirus samiri), cytomegalovirus (CMV) or lentivirus;

asthma;

osteoporosis; (low bone mineral density);

tumor growth;

rheumatoid arthritis;

organ transplant rejection and/or delayed graft or organ function, e.g. in renal transplant patients;

a disorder characterised by an elevated TNF-α level;

psoriasis;

skin wounds;

disorders caused by intracellular parasites such as malaria or tuberculosis;

allergies; or

Alzheimer's disease.

According to this invention, further inflammatory disorders include:

ALS;

fibrosis (particularly pulmonary fibrosis, but not limited to fibrosis in the lung);

the formation of adhesions (particularly in the peritoneum and pelvic region).

antigen induced recall response immune response suppression

These clinical indications fall under the general definition of inflammatory disorders or disorders characterized by elevated TNFα levels.

Where legally permissible, the invention also provides a method of treatment, amelioration or prophylaxis of the symptoms of an inflammatory disease (including an adverse inflammatory reaction to any agent) by the administration to a patient of an anti-inflammatory amount of a compound, composition or medicament as claimed herein.

Administration of a medicament according to the invention can be carried out by topical, oral, parenteral route, by intramuscular injection, etc.

The administration dose envisaged for a medicament according to the invention is comprised between 0.1 mg and 10 g depending on the type of active compound used.

Also envisaged is the generation of a library of two or more compounds described herein, where all the Compounds have a structure according to the general formula (I), and hence where the compounds should have anti-inflammatory activity. The said library may then be screened for compounds which are particularly active in a particular assay, or which possess a particular collection of physical, biological and/or pharmaceutical properties, and are therefore particularly suited to a particular application.

According to the invention, the compounds of general formula (I) or (I') can be prepared using the processes described hereafter.

Preparation of the Compounds of General Formula (I) or (I')

All the compounds of general formula (I) or (I') can be prepared easily according to general methods known to the person skilled in the art.

Nevertheless, the following preferred synthetic route is proposed:

Diagram 1

STEP 1

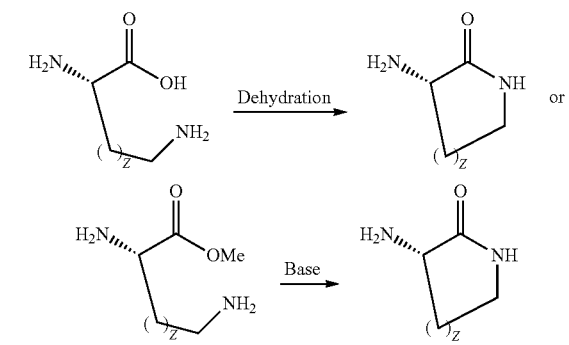

STEP 2

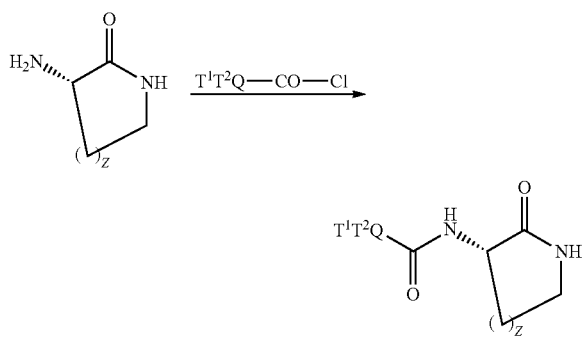

In the first step, 3-aminolactams are synthesised either by direct dehydration of the appropriate diaminocarboxylic acid (2,4-diaminobutyric acid to yield 5-ring aminolactam, ornithine to yield a 6-ring lactam, lysine to yield a 7-ring lactam or 2,7-diaminoheptanoic acid to yield an 8-ring lactam) as previously described [Synthesis, 1978, 614-616], or else by base-mediated cyclisation of esters of the same diaminocarboxylic acids, as previously described using lysine methyl ester [J. Org. Chem., 1979, 44, 4841-4847] for the 7-ring lactam.

In the second step, the 3-aminolactam product is reacted with an activated acid equivalent (for example, an appropriate acid chloride, as previously described for 7-ring aminolactams [J. Med. Chem., 2005, 48, 867-74]).

The above reaction may be carried out at ambient temperature (about 25° C.) or more generally at a temperature between 20 and 50° C.

A wide variety of appropriate activated acid equivalents, when reacted with a 3-aminolactam in accordance with step 2 of the synthesis outlined in Diagram 1, will yield compounds according to the invention. Many of the acids (which can then be subsequently activated, for example as acid chlorides or using conventional amide bond synthesis reagents such as 1-hydroxybenzotriazole monohydrate and carbonyl diimidazole) are commercially available (for example, 1-methylcyclohexyl carboxylic acid is readily available from commercial suppliers). The remaining activated acid equivalents, or the carboxylic acids or carboxylate esters from which they are readily derived, may be synthesised using a range of methods well known in the art.

For example, for the synthesis of 3-(1'-methyl-2'-hydroxycyclohexylcarbonylamino) caprolactam, 1-methyl-2-hydroxycyclohexyl carboxylic acid could be synthesised by the methylation of commercially available 2-oxocyclohexyl carboxylic acid ethyl ester, for example by deprotonation (enolisation) using potassium tert-butoxide then methylation by iodomethane, followed by reduction (for example with sodium borohydride). The resultant ethyl ester of 1-methyl-2-hydroxycyclohexane carboxylic acid may then be readily converted to the free acid or activated acid equivalent using methods well known in the art.

It will be obvious to those skilled in the art that protecting groups may have to be used during the amide bond formation in step 2 of the schema in Diagram 1, in the event that the appropriate acid has one or more substituents which are reactive under the conditions of forming the activated acid equivalent, or its subsequent reaction with 3-aminolactam to form the amide. Selection of appropriate protection groups, as well as the most appropriate activated acid equivalent, for a given reaction is in accordance with well established principles, known to those skilled in the art.

For example, for the synthesis of 3-(1'-methyl-2'-hydroxycyclohexylcarbonylamino) caprolactam, the hydroxyl group must be protected during amide bond formation. For example, the 1-methyl-2-hydroxycyclohexyl carboxylate (as the ethyl ester) may be reacted with 3,4-dihydro-2H-pyran in the presence of para-toluene-sulphonic acid, to yield Ethyl 1-Methyl-2-(tetrahydropyran-2'-yloxy)-cyclohexane carboxylate. After acid hydrolysis of the ester, the resultant protected acid may then be activated, for example by reaction with 1-hydroxybenzotriazole monohydrate and carbonyl diimidazole to form the activated HoBT ester. This then reacts with an appropriate 3-aminolactam to form the amide bond in step 2 of Diagram 1. Subsequently, the protecting group could be removed, for example by acidic methanolysis (using acetyl chloride in methanol) to yield 3-(1'methyl-2'-hydroxycyclohexylcarbonylamino)-caprolactam.

DEFINITIONS

The term "about" refers to an interval around the considered value. As used in this patent application, "about X" means an interval from X minus 10% of X to X plus 10% of X, and preferably an interval from X minus 5% of X to X plus 5% of X.

The use of a numerical range in this description is intended unambiguously to include within the scope of the invention all individual integers within the range and all the combinations of upper and lower limit numbers within the broadest scope of the given range. Hence, for example, the range of 1 to 20 carbon atoms specified in respect of (inter alia) formula I is intended to include all integers between 4 and 20 and all sub-ranges of each combination of upper and lower numbers, whether exemplified explicitly or not.

As used herein, the term "comprising" is to be read as meaning both comprising and consisting of: Consequently, where the invention relates to a "pharmaceutical composition comprising as active ingredient" a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference (where legally permissible).

The following examples are presented in order to illustrate the above procedures and should in no way be considered to limit the scope of the invention.

FIGURES

FIG. 1 shows the chemical structure of examples of compounds according to the invention.

EXAMPLES

Example 1

—(S)-3-(2'-hydroxy-1'-methylcyclohexanecarbonyl) amino-caprolactam (as mixture of stereoisomers at the 1' and 2' positions): 1-methyl-2-(tetrahydropyran-2'-yloxy)-cyclohexane carboxylic acid (see below for synthesis and characterisation, 1.87 g, 7.30 mmol), 1-hydroxybenzotriazole monohydrate (7 mmol) and carbonyl diimidazole (7 mmol) were dissolved in THF (50 ml) and the reaction was heated at reflux for 4 hours. After the reaction was cooled to ambient temperature, a solution of (S,S)-3-amino-caprolactam hydro-pyrrolidine-5-carboxylate (8 mmol) and $Na_2CO_3$ (24 mmol) in water (50 ml) was added and the reaction was stirred for 18 hours. The THF was then removed from the reaction by distillation in vacuo and the aqueous layer was extracted with ethyl acetate. The ethyl acetate layer was washed with pH2 aqueous buffer and dilute aqueous potassium hydroxide, and was dried over $Na_2SO_4$ and reduced in vacuo. The residue was dissolved in MeOH, and acetyl chloride (1 ml) was added. The reaction was stirred at ambient temperature for 18 hours, and then reduced in metro to give a residue This crude product was purified by silica column chromatography (EtOAc:hexanes 1:3 to MeOH:EtOAc 1:19) to give the lactam (as a diastereoisomeric mixture) as a gummy solid (1.26 g, 65%, based on cyclohexane acid); $v_{max}/cm^{-1}$ 3277 (NH), 1669, 1624 (CO), 1512 (NH); $\delta_H$ (500 MHz, $CDCl_3$) 7.78-7.62 (1H, m, NH, 3 isomers), 7.38 (1H, br s, NH, 1 isomer), 6.78-6.48 (1H, m, NH, 4 isomers), 4.54-4.28 (2H, NCH+OH, 4 isomers), 3.83-3.66 (1H, m, CHOH, 2 isomers), 3.42-3.33 (1H, m, CHOH, 2 isomers), 3.29-3.16 (2H, m, $NCH_2$, 4 isomers), 2.32-1.92 (3H, m, lactam CH and cyclohexyl CH, 4 isomers), 1.86-1.71 (4H, m, lactam CH and cyclohexyl CH, 4 isomers), 1.56-1.09 (10H, m, lactam CH and cyclohexyl CH, 4 isomers and Me); $\delta_C$, (125 MHz, $CDCl_3$) 178.9, 176.9, 176.8, 176.7, 175.7, 175.6 (CO), 72.7, 72.6 (CHOH), 52.1, 51.9, 51.8 (NCH), 46.8, 46.7, 46.1, 45.8 ($CH_3CCO$), 42.0 ($NCH_2$), 35.3, 35.1, 33.2, 33.0, 32.1, 32.0 (cyclohexyl $CH_2$), 31.5, 31.4, 31.3, 31.1, 29.1, 28.8, 27.9 (lactam $CH_2$), 25.2 ($CH_3$), 24.3, 24.2, 24.1, 22.6, 21.0, 20.9, 20.8 (cyclohexyl $CH_2$), 15.4 ($CH_3$); m/z ($MH^+ C_{14}H_{25}N_2O_3$ requires 269.1865) 269.1852, ($MNa^+ C_{14}H_{24}N_2O_3Na$ requires 291.1685) 291.1671.

For the synthesis of the protected acid side-chain 1-methyl-2-(tetrahydropyran-2'-yloxy)-cyclohexane carboxylic acid, ethyl 2-oxocyclohexane carboxylate (8.5 g, 50 mmol) was dissolved in dry THF at ambient temperature under $N_2$. Potassium tert-butoxide (75 mmol) was added slowly and the reaction was stirred for 5 minutes. Iodomethane (100 mmol) was then added and the reaction was stirred at ambient temperature for 1 hour. The reaction solvent was removed under reduced pressure and the residue was partitioned between water and hexane. The organic layer was dried over sodium sulfate and reduced under reduced pressure to give racemic ethyl 1-methyl-2-oxo-cyclohexanecarboxylate as a colourless oil (8.11 g 88%); $\delta_H$ (400 MHz, $CDCl_3$) 4.25-4.12 (2H, m, $OCH_2CH_3$), 2.55-2.40 (3H, m, $CH_2CO$ and one other cyclohexane peak), 2.05-1.95 (1H, m, cyclohexane), 1.77-1.57 (3H, m, cyclohexane), 1.50-1.40 (1H, m, cyclohexane), 1.28 (3H, s, $CCH_3$) and 1.25 (1H, t, J 7, $CH_2CH_3$). Ethyl 1-methyl-2-oxo-cyclohexanecarboxylate (5.52 g, 30 mmol) was dissolved in ethanol (100 ml) at ambient temperature and sodium borohydride (1.14 g, 30 mmol) was added slowly. After 1 hour the reaction solvent was removed in vacuo and the residue was partitioned between water and dichloromethane. The organic extracts were dried over sodium sulphate and reduced to give ethyl 2-hydroxy-1-methylcyclohexanecarboxylate as a mixture of diastereoisomers (5.37 g 96%). This material was then protected and the ester hydrolysed as follows: Ethyl 2-hydroxy-1-methylcylcohexanecarboxylate (16.7 mmol) was dissolved in dichloromethane along with 3,4-dihydro-2H-pyran (17 mmol) and para-toluene-sulphonic acid (5 mg), and the reaction was stirred at ambient temperature for 16 hours. The solvent was removed under reduced pressure to give a residue to which was added ethanol (40 ml), water (10 ml) and potassium hydroxide (20 mmol). The mixture was heated at reflux overnight and allowed to cool. The reaction solvent was removed under reduced pressure and the residue was partioned between water and diethyl ether. The aqueous layer was acidified to pH 2 and then extracted with diethyl ether. This ether layer was dried over sodium sulphate and reduced in vacuo to give crude 1-methyl-2-(tetrahydropyran-2'-yloxy)-cyclohexane carboxylic acid (2.52 g) as a mixture of diastereoisomers. This material was used in the synthesis of (S)-3-(2'-hydroxy-1'-methylcyclohexanecarbonyl)amino-caprolactam above Example 2

—(S)-3-(1'-Phenyleyclohexanecarbonyl)amino-caprolactam (S,S)-3-amino-caprolactam hydro-pyrrolidine-5-carboxylate (2 mmol) and $Na_2CO_3$ (6 mmol) in water (25 ml) were added to a solution of 1-phenylcyclohexanecarbonyl chloride (2 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2CO_3$ and reduced in vacuo. The residue was purified by silica column chromatography (from EtOAc/hexane to MeOH/EtOAc) to give the lactam as an amorphous solid (401 mg, 64%); $v_{max}/cm^{-1}$ 13270 (NH), 1639 (CO), 1432 (NH); $\delta_H$ (500 MHz, $CDCl_3$) 7.42-7.37 (2H, m, Ph), 7.33-7.27 (2H, m, Ph), 7.22-7.17 (1H, m, Ph), 6.90 (1H, d, J 5.5, CHNH), 6.47-6.20 (1H, br s, $CH_2NH$), 4.41 (1H, dd, J 11, 5.5, CHNH), 3.25-3.09 (2H, m, $CH_2NH$), 2.35-2.25 (2H, m, cyclohexane CH), 2.00-1.87 (4H, m, lactam ring CH and cyclohexane CH), 1.82-1.69 (2H, m, lactam ring CH), 1.61-1.47 (5H, m, cyclohexane CH) and 1.40-1.25 (3H, m, lactam ring CH and cyclohexane CH); $\delta_C$ (125 MHz, $CDCl_3$) 175.7, 174.6 (CO), 143.8 (ipso-Ph), 128.6 (ortho- or meta-Ph), 126.6 (para-Ph), 126.3 (ortho- or meta-Ph), 52.2 (NH-CHCO), 50.5 (C quat), 42.0 ($NCH_2$), 34.4, 34.3, 31.2, 28.8, 27.9, 25.8, 23.1 (×2) ($CH_2$); m/z ($MH^+ C_{19}H_{27}N_2O_2$ requires 315.2073) 315.2060.

Example 3

(S)-3-(1"-Phenylcyclohexanecarbonyl)amino-tetrahydropyridin-2-one (S)-3-Amino-tetrahydropyridin-2-one hydrochloride (2 mmol) and $Na_2CO_3$ (6 mmol) in water (25 ml) were added to a solution of 1-phenylcyclohexanecarbonyl chloride (2 mmol) in dichloromethane (25 ml) at ambient temperature and the reaction was stirred for 12 hours. The organic layer was then separated and the aqueous phase was extracted with additional dichloromethane (2×25 ml). The combined organic layers were dried over $Na_2SO_4$ and reduced in vacuo. The residue was purified crystallisation from hexanes to give the lactam as a solid (327 mg, 54%); $v_{max}/cm^{-1}$ 13283, 3196 (NH), 1663, 1650 (CO), 1516 (NH); $\delta_H$ (500 MHz, $CDCl_3$) 7.43-7.35 (2H, m, Ph), 7.35-7.26 (2H, m, Ph), 7.24-7.17 (1H, m, Ph), 6.48-5.73 (2H, br m, NH), 4.09 (1H, dt, J 11, 5.5, CHNH), 3.30-3.17 (2H, m, $CH_2NH$), 2.52-2.37 (1H, m, lactam CH), 2.33-2.21 (2H, m, cyclohexane CH), 2.05-1.76 (4H, m, lactam ring CH and cyclohexane CH), 1.65-1.48 (5H, m, cyclohexane CH), and 1.43-1.27 (2H, m, lactam ring CH and cyclohexane CH); $\delta_C$ (125 MHz, $CDCl_3$) 175.8, 171.8 (CO) 143.8 (ipso-Ph), 128.6 (ortho- or meta-Ph), 126.6 (para-Ph), 126.4 (ortho- or meta-Ph), 50.8 (NHCHCO), 50.5 (C quat), 41.4 ($NCH_2$), 34.8, 34.4, 26.7, 25.8, 23.0 (×2), 21.0 ($CH_2$);

m/z (MH+ $C_{18}H_{25}N_2O_2$ requires 301.1916) 301.1905, (MNa+ $C_{18}H_{24}N_2O_2Na$ requires 323.1735) 323.1725.

Example 4

(S)-3-(cis-4''-tert-Butyl-1'-methyl-1'-cyclohexanecarbonyl)amino-caprolactam cis-4'-Butyl-1-methyl-1-cyclohexanecarboxlic acid (synthesised according to *Aust. J. Chem.* 1970, 1005) (328 mg, 1.66 mmol) was dissolved in dichloromethane (10 ml) along with oxalyl chloride (1 ml) and dimethyl formamide (1 drop). The reaction was stirred at ambient temperature for 1 hour, and then the dichloromethane and excess oxalyl chloride were removed under reduced pressure. The crude acid chloride residue was dissolved in dichloromethane (10 ml) and the solution was added to a solution of (S,S)-3-amino-caprolactam hydro-pyrrolidine-5-carboxylate (2 mmol) and $Na_2CO_3$ (6 mmol) in water (10 ml) and the reaction was stirred for 18 hours. The organic layer was then separated and the aqueous phase was extracted with additional dichloromethane (2×25 ml). The combined organic layers were dried over $Na_2SO_4$ and reduced in vacuo. The residue was purified by recrystallisation from heptane to give the lactam (297 mg, 58%); $v_{max}/cm^{-1}$ 13390, 3233 (NH), 1676, 1625 (CO), 1516 (NH); $\delta_H$ (500 MHz, $CDCl_3$) 7.14 (1H, d, J5.5, CHNH), 6.50-6.30 (1H, br m, $CH_2NH$), 4.53 (1H, dd, J11, 5.5, CHNH), 3.32-3.17 (2H, m, $CH_2NH$), 2.24-2.14 (2H, m, cyclohexane CH), 2.07-1.97 (2H, m, lactam ring CH), 1.87-1.75 (2H, m, lactam ring CH), 1.67-1.58 (2H, m, cyclohexane CH), 1.48-1.31 (2H, m, lactam ring CH), 1.20-0.88 (8H, m, cyclohexane CH×5 and $CH_3$) and 0.77 (9H, s, $C(CH_3)$); $\delta_C$ (125 MHz, $CDCl_3$) 176.0 (CO×2), 52.0 (NHCHCO), 47.6 (CH), 42.9 (C quat), 42.1, 36.7, 36.5 ($CH_2$), 32.3 (C quat), 31.6 ($CH_2$), 29.4 ($CH_3$), 28.9, 28.0 ($CH_2$), 27.5 (($CH_3)_3$), 24.5 ($CH_2$×2); m/z (MNa+ $C_{18}H_{32}N_2O_2Na$ requires 331.2361) 331.2352.

Example 5

(S)-3-(1'-Methylcyclohexanecarbonyl)amino-tetrahydropyridin-2-one (S)-3-Amino-tetrahydropyridin-2-one hydrochloride (2 mmol) and $Na_2CO_3$ (6 mmol) in water (25 ml) were added to a solution of 1-methylcyclohexanecarbonyl chloride (2 mmol) in dichloromethane (25 ml) at ambient temperature and the reaction was stirred for 18 hours. The organic layer was then separated and the aqueous phase was extracted with additional dichloromethane. The combined organic layers were dried over $Na_2SO_4$ and reduced in vacuo. The residue was purified by silica column chromatography (EtOAc:hexanes 1:3 to MeOH:EtOAc 1:19) to give as an amorphous solid (199 mg, 42%); $v_{max}/cm^{-1}$ 3335, 3269 (NH), 1650, 1621 (CO), 1529 (NH); $\delta_H$ (500 MHz, $CDCl_3$) 6.65 (1H, br d, J 5, NH), 6.59 (1H, br s, NH), 4.18 (1H, dt, J 11.5, 5.5, CHNH), 3.30 (2H, td, J6.5, 2.5, $CH_2NH$), 2.52 (1H, ddt, J 13, 5.5, 4.5, lactam $CH_2$), 1.92-1.83 (4H, m, 2× lactam CH and 2× cyclohexane $CH_2$), 1.55-1.23 (9H, m, lactam CH and 8× cyclohexane $CH_2$) and 1.11 (3H, s, $CH_3$); $\delta_C$ (125 MHz, $CDCl_3$) 178.0, 172.3 (CO), 50.4 (NHCHCO), 42.6 ($CH_3C$ quat), 41.5, 35.6, 35.5, 27.0 ($CH_2$), 26.3 ($CH_3$), 25.7, 22.8 (×2), 20.9 ($CH_2$): m/z (MNa+ $C_{13}H_{22}N_2O_2Na$ requires 261.1579) 261.1570.

Example 6

(S)-3-(1'-Methylcyclohexanecarbonyl)amino-pyrrolidin-2-one (S)-3-Amino-pyrrolidin-2-one (2 mmol) and $Na_2CO_3$ (4 mmol) in water (25 ml) were added to a solution 1-methyl-cyclohexanecarbonyl chloride (2 mmol) in dichloromethane (25 ml) at ambient temperature and the reaction was stirred for 18 hours. The organic layer was then separated and the aqueous phase was extracted with additional dichloromethane. The combined organic layers were dried over $Na_2SO_4$ and reduced in vacuo. The residue was purified by silica column chromatography (EtOAc:hexanes 1:3 to MeOH:EtOAc 1:19) to give the lactam as an amorphous solid (276 mg, 62%); $v_{max}/cm^{-1}$ 3321 (NH), 1698, 1633 (CO), 1526 (NH); $\delta_H$ (400 MHz, $CDCl_3$) 6.98 (1H, br s, NH), 6.34 (1H, br s, NH), 4.26 (1H, ddd, J 10.5, 8.5, 5, CHNH), 3.41-3.26 (2H, m, $CH_2NH$), 2.79-2.67 (1H, m, $CHCH_2N$), 1.92-1.77 (3H, m, $CH_2CH_2N$ and 2× cyclohexane $CH_2$), 1.58-1.18 (8H, m, 8× cyclohexane $CH_2$) and 1.12 (3H, s, $CH_3$); $\delta_C$ (100 MHz, $CDCl_3$) 178.6, 176.3 (CO), 50.9 (NHCHCO), 42.6 (CCO), 39.4, 35.5 (×2), 30.0 ($CH_2$), 26.2 ($CH_3$), 25.7, 22.8 (×2) ($CH_2$); m/z (MH+ $C_{12}H_{21}N_2O_2$ requires 225.1603) 225.1596, (MNa+ $C_{12}H_{20}N_2O_2Na$ requires 247.1422) 147.1417.

Example 7

(S)-3-(1'((tert-Butoxycarbonylamino)cyclopentanecarbonyl)amino-caprolactam 1-(tert-Butoxycarbonylamino)cyclopentanecarboxylic acid (2 mmol) and triethylamine (2 mmol) were dissolved in THF (20 ml), and 4-(4,6-dimethoxy[1,3,5]triazin-2-yl)-4-methyl-morpholinium chloride (1.40 mmol) was added. The reaction was stirred for 16 hours and then (S,S)-3-amino-caprolactam hydro-pyrrolidine-5-carboxylate (2 mmol) and $Na_2CO_3$ (6 mmol) in water (20 ml) was added and the reaction was stirred for 18 hours. The reaction solvent was removed in vacuo. The residue was partitioned between ethyl acetate and water. The ethyl acetate layer was washed with dilute aqueous HCl and dilute aqueous NaOH, and then dried over $Na_2SO_4$. The solvent was removed in vacuo and the residue was recrystallised from ethyl acetate/hexane to give the lactam as a white solid (407 mg, 60%); $v_{max}/cm^{-1}$ 3380, 3280 (NH), 1693, 1664, 1644 (CO), 1527, 1497 (NH); $\delta_H$ (400 MHz, $CDCl_3$) 7.53 (1H, d, J 5, NH), 6.90-6.40 (1H, br m, NH), 5.30-4.90 (1H, br m, NH), 4.46 (1H, br dd, J 9.5, 6, CHNH), 3.28-3.13 (2H, m, $CH_2NH$), 2.32-2.12 (2H, m, cyclopentane $CH_2$), 2.05 (1H, br d, J 13.5, lactam $CH_2$), 1.99-1.91 (1H, m, lactam $CH_2$), 1.89-1.63 (8H, m, 6× cyclopentane $CH_2$ and 2× lactam $CH_2$) and 1.43-1.33 (11H, m, 2× lactam $CH_2$ and $(CH_3)_3$); $\delta_C$ (100 MHz, $CDCl_3$) 175.7, 173.4 (CO amide), 154.4 (CO carbamate), 79.8 ($OMe_3$), 66.7 (NCCO), 52.3 (NHCHCO), 42.0 ($NCH_2$), 37.3, 37.1, 31.3, 28.9 ($CH_2$), 28.3 (×4) ($CH_2$ and 3×$CH_3$), 28.0, 24.5 ($CH_2$); m/z (MNa+ $C_{17}H_{29}N_3O_4Na$ requires 362.2056) 362.2045, (MH+ $C_{17}H_{30}N_3O_4$ requires 340.2236) 340.2228.

Example 8

(S)-3-(3'-hydroxy-1'-adamantanecarbonyl)amino-caprolactam

3-Hydroxy adamantane-1-carboxylic acid (2 mmol) and 1-hydroxybenzotriazole monohydrate (2 mmol) were dissolved in THF/$CH_2Cl_2$ (2:3 v/v, 50 ml). 1-[3-(Dimethylamino)propyl]-3-ethylcarbodiimide hydrochloride (2 mmol) was added and the reaction was stirred at ambient temperature for 4 hours. A solution of (S,S)-3-amino-caprolactam hydro-pyrrolidine-5-carboxylate 2 (2 mmol) and $Na_2CO_3$ (6 mmol) in water (15 ml) was added and the reaction was stirred for 18 hours. The reaction solvent was then removed in vacuo and the residue was partitioned between water and dichloromethane. The organic layer was washed with pH 2 buffer (0.5 M $Na_2SO_4$/0.5 M $NaHSO_4$) and dilute aqueous sodium hydroxide, and then dried over $Na_2SO_4$ and reduced in vacuo. The residue was recrystallised (hexanes) to give the lactam as a white solid (277 mg, 45%); m.p. (hexanes) 197-199° C.; $[\alpha]_D^{25}$ (c=0.5, $CHCl_3$)+29.9; $v_{max}$/cm$^{-1}$ 3443 (OH), 3391, 3296 (NH), 1646, 1624 (CO), 1502 (NH); $\delta_H$ (500 MHz, $CDCl_3$) 7.08 (1H, d, J 5.5, CHNH), 6.57 (1H, br t, J 6, $CH_2NH$), 4.43 (1H, ddd, J 11, 5.5, 1.5, CHNH), 3.28-3.16 (2H, m, $CH_2NH$), 2.30 (1H, br s, OH), 2.24 (2H, br s, adamantane CH), 2.02-191 (2H, m, 2× lactam ring CH), 1.85-1.75 (4H, m, 2× ring CH+2× adamantane CH), 1.73 (4H, br s, adamantane CH), 1.71-1.63 (4H, m, adamantane CH), 1.55 (2H, br s, 2× adamantane CH) and 1.45-1.31 (2H, m, 2× ring CH); $\delta_C$ (125 MHz, $CDCl_3$) 175.9, 175.7 (CO), 68.3 (COH), 51.9 (NHCHCO), 46.6, 44.2 (×2) (3×$CH_2$ adamantane), 44.0 (CCO), 42.1 ($CH_2N$), 37.9 (×2), 35.0 (3×$CH_2$ adamantane), 31.5 ($CH_2$ lactam), 30.4 (2×CH adamantane), 28.8, 27.9 ($CH_2$ lactam); m/z ($MH^+$ $C_{17}H_{27}N_2O_3$ requires 307.2022) 307.2024, ($MNa^+$ $C_{17}H_{26}N_2O_3Na$ requires 329.1841) 329.1847.

Pharmacological Study of the Products of the Invention
Inhibition of MCP-1 Induced Leukocyte Migration
Assay Principle The biological activity of the compounds of the current invention may be demonstrated using any of a broad range of functional assays of leukocyte migration in vitro, including but not limited to Boyden chamber and related transwell migration assays, under-agarose migration assays and direct visualisation chambers such as the Dunn Chamber.

For example, to demonstrate the inhibition of leukocyte migration in response to chemokines (but not other chemoattractants) the 96-well format micro transwell assay system from Neuroprobe (Gaithersburg, Md., USA) has been used. In principle, this assay consists of two chambers separated by a porous membrane. The chemoattractant is placed in the lower compartment and the cells are placed in the upper compartment.

After incubation for a period at 37° C. the cells move towards the chemoattractant, and the number of cells in the lower compartment is proportional to the chemoattractant activity (relative to a series of controls).

This assay can be used with a range of different leukocyte populations. For example, freshly prepared human peripheral blood leukocytes may used. Alternatively, leukocyte subsets may be prepared, including polymorphonuclear cells or lymphocytes or monocytes using methods well known to those skilled in the art such as density gradient centrifugation or magnetic bead separations. Alternatively, immortal cell lines which have been extensively validated as models of human peripheral blood leukocytes may be used, including, but not limited to THP-1 cells as a model of monocytes or Jurkat cells as model of naïve T cells.

Although a range of conditions for the assay are acceptable to demonstrate the inhibition of chemokine-induced leukocyte migration, a specific example is hereby provided.

Materials

The transwell migration systems are manufactured by Neuroprobe, Gaithersburg, Md., USA.

The plates used are ChemoTx plates (Neuroprobe 101-8) and 30 µl clear plates (Neuroprobe MP30).

Geys' Balanced Salt Solution is purchased from Sigma (Sigma G-9779).

Fatty acid-free BSA is purchased from Sigma (Sigma A-8806).

MTT, i.e. 3-(4,5-dimethylthiazol-2-yl)-2,5-diphenyltetrazolium bromide, is purchased from Sigma (Sigma M-5655).

RPMI-1640 without phenol red is purchased from Sigma (Sigma R-8755).

The THP-1 cell line (European Cell culture Collection) were used as the leukocyte cell population.

Test Protocol

The following procedure is used for testing the invention compounds for MCP-1 induced leukocyte migration:

First, the cell suspension to be placed in the upper compartment is prepared. The THP-1 cells are pelleted by centrifugation (770×g; 4 mins) and washed with Geys Balanced Salt Solution with 1 mg/ml BSA (GBSS+BSA). This wash is then repeated, and the cells repelleted before being resuspended in a small volume of GBSS+BSA for counting, for example using a standard haemocytometer.

The volume of GBSS+BSA is then adjusted depending on the number of cells present so that the cells are at final density of $4.45 \times 10^6$ cells per ml of GBSS+BSA. This ensures that there are 100,000 THP-1 cells in each 25 µl of the solution that will be placed in the upper chamber of the plate.

To test a single compound for its ability to inhibit MCP-1 induced migration, it is necessary to prepare two lots of cells. The suspension of THP-1 cells at $4.45 \times 10^6$ cells/ml is divided into two pots. To one pot the inhibitor under test is added at an appropriate final concentration, in an appropriate vehicle (for example at 1 µM in not more than 1% DMSO). To the second pot an equal volume of GBSS+BSA plus vehicle as appropriate (e.g. not more than 1% DMSO) is added to act as a control.

Next, the chemoattractant solution to be placed in the lower compartment is prepared. MCP-1 is diluted in GBSS+BSA to give a final concentration of 25 ng/ml. This is divided into two pots, as for the cell suspension. To one pot, the test compound is added to the same final concentration as was added to the cell suspension, while to the other pot an equal volume of GBSS+BSA plus vehicle as appropriate (e.g. not more than 1% DMSO) is added.

Note that the volume of liquid that needs to be added to make the addition of the text compound needs to be taken into account, when establishing the final concentration of MCP-1 in the solution for the lower compartment and the final concentration of cells in the upper compartment.

Once the chemoattractant solutions for the lower wells and cell solutions for the upper chambers have been prepared, the migration chamber should be assembled. Place 29 µA of the appropriate chemoattractant solution into the lower well of the chamber. Assays should be performed with at least triplicate determinations of each condition. Once all the lower chambers have been filled, apply the pious membrane to the chamber in accordance with the manufacturer's instructions. Finally, apply 25 µl of the appropriate cell solution to each upper chamber. A plastic lid is placed over the entire apparatus to prevent evaporation.

The assembled chamber is incubated at 37° C., 5% $CO_2$, for 2 hours. A suspension of cells in GBSS+BSA is also incubated under identical conditions in a tube: these cells will be used to construct a standard curve for determining the number of cells that have migrated to the lower chamber under each condition.

At the end of the incubation, the liquid cell suspension is gently removed from the upper chamber, and 20 µl of ice-cold 20 mM EDTA in PBS is added to the upper chamber, and the apparatus is incubated at 4° C. for 15 mins. This procedure causes any cells adhering to the underside of the membrane to fall into the lower chamber.

After this incubation the filter is carefully flushed with GBSS+BSA to wash off the EDTA, and then the filter is removed.

The number of cells migrated into the lower chamber under each condition can then be determined by a number of methods, including direct counting, labelling with fluorescent or radioactive markers or through the use of a vital dye. Typically, we utilise the vital dye MTT. 3 μl of stock MTT solution are added to each well, and then the plate is incubated at 37° C. for 1-2 hours during which time dehydrogenase enzymes within the cells convert the soluble MTT to an insoluble blue formazan product that can be quantified spectrophotometrically.

In parallel, an 8-point standard curve is set up. Starting with the number of cells added to each upper chamber (100,000) and going down in 2-fold serial dilutions in GBSS+BSA, the cells are added to a plate in 25 μl, with 3 μl of MTT stock solution added. The standard curve plate is incubated along side the migration plate.

At the end of this incubation, the liquid is carefully removed from the lower chambers, taking care not to disturb the precipitated formazan product. After allowing to air dry briefly, 20 μl of DMSO is added to each lower chamber to solubilise the blue dye, and absorbance at 595 nm is determined using a 96-well plate reader. The absorbance of each well is then interpolated to the standard curve to estimate the number of cells in each lower chamber.

The MCP-1 stimulated migration is determined by subtracting the average number of cells that reached the lower compartment in wells where no MCP-1 was added from the average number of cells that reached the lower compartment where MCP-1 was present at 25 ng/ml.

The impact of the test substance is calculated by comparing the MCP-1-induced migration which occurred in the presence or absence of various concentrations of the test substance. Typically, the inhibition of migration is expressed as a percentage of the total MCP-1 induced migration which was blocked by the presence of the compound. For most compounds, a dose-response graph is constructed by determining the inhibition of MCP-1 induced migration which occurs at a range of different compound concentrations (typically ranging from 1 nM to 1 μM or higher in the case of poorly active compounds). The inhibitory activity of each compound is then expressed as the concentration of compound required to reduce the MCP-1-induced migration by 50% (the $ED_{50}$ concentration).

Results

The compounds of examples 1 to 7 were tested and were shown to have an $ED_{50}$ of 100 nM or less in this test.

Enantioselectivity

The (S)- and (R)-enantiomers (at the 3 position of the aminolactam ring) of two different members of the series can be synthesised to determine whether the biological activity showed enantioselectivity.

The dose-response curves for each of the compounds as inhibitors of MCP-1 induced THP-1 cell migration can be determined using the transwell migration assay.

For the application of the compounds of the present invention as anti-inflammatory agents in vivo it is preferable to use the pure (S)-enantiomer of the compound, rather than the racemic mixture of the two enantiomers or the pure (R)-enantiomer.

The invention claimed is:

1. A method to treat or ameliorate an inflammatory disorder or a symptom thereof, comprising administering to a patient an effective amount of a compound of general formula (I) or a pharmaceutically acceptable salt thereof:

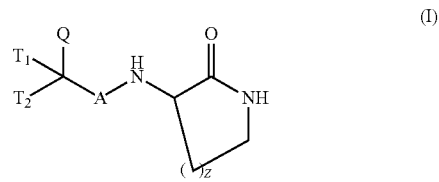

but excluding (S)-3-(1'-methylcyclohexylcarbonylamino)-caprolactam: wherein z is 1, 2, 3 or 4;

A is —CO— or —$SO_2$—;

Q is linear or branched alkyl, alkenyl, alkynyl, alkoxy, oxyalkyl, aminoalkyl, alkylamino, alkylaminoalkyl, haloalkyl, aryl or substituted aryl, or tert-Butoxycarbonylamino;

$T^1$ and $T^2$ together constitute a cycloalkyl, cycloalkenyl or polycycloalkyl radical composed of n additional carbon atoms, where n is between 2 and 7;

and each hydrogen atom bonded to the carbon atoms in the ring generated by $T^1$ and $T^2$ may be independently substituted by a group $R^1$, where $R^1$ is independently selected from an alkyl, haloalkyl, alkoxy, haloalkoxy, alkenyl, alkynyl or alkylamino radical of 1 to 20 carbon atoms;

or each $R^1$ is independently selected from fluoro, chloro, bromo, iodo, hydroxy, oxyalkyl, amino, aminoalkyl or aminodialkyl radical.

2. A method to treat or ameliorate an inflammatory disorder or a symptom thereof, comprising administering to a patient an effective amount of a compound of general formula (I') or a pharmaceutically acceptable salt thereof:

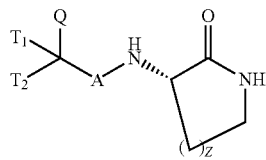

(I')

wherein z is 1, 2, 3, or 4;

A is —CO— or —SO$_2$—;

Q is linear or branched alkyl, alkenyl, alkynyl, alkoxy, oxyalkyl, aminoalkyl, alkylamino, alkylaminoalkyl, haloalkyl, aryl or substituted aryl, or tert-butoxycarbonylamino;

$T^1$ and $T^2$ together constitute a cycloalkyl, cycloalkenyl or polycycloalkyl radical composed of n additional carbon atoms, where n is between 2 and 7;

and each hydrogen atom bonded to the carbon atoms in the ring generated by $T^1$ and $T^2$ may be independently substituted by a group $R^1$, where $R^1$ is independently selected from an alkyl, haloalkyl, alkoxy, haloalkoxy, alkenyl, alkynyl or alkylamino radical of 1 to 20 carbon atoms;

or each $R^1$ is independently selected from fluoro, chloro, bromo, iodo, hydroxy, oxyalkyl, amino, aminoalkyl or aminodialkyl radical.

3. The method of claim 1, wherein the ring or rings specified by $T^1$ and $T^2$ constrain the bond angles at the alpha-carbon to be essentially tetrahedral (i.e, sp3 hybrid bonds).

4. The method of claim 1, wherein A is —CO—.

5. The method of claim 1, wherein Q is methyl.

6. The method of claim 1, wherein Q is phenyl or substituted phenyl.

7. The method of claim 1, wherein A is —CO— and Q is methyl.

8. The method of claim 1, wherein A is —CO— and Q is phenyl or substituted phenyl.

9. The method of claim 1, wherein z is 2 or 3.

10. The method of claim 1, wherein z is 3.

11. The method of claim 1, wherein z is 3 and A is —CO—.

12. The method of claim 1, wherein z is 3 and A is —CO— and Q is methyl.

13. The method of claim 1, wherein z is 3 and A is —CO— and Q is phenyl or substituted phenyl.

14. The method of claim 1, wherein $T^1$ and $T^2$ together constitute a cyclohexyl, substituted cyclohexyl, cyclohexenyl or substituted cyclohexenyl radical.

15. The method of claim 1, wherein $T^1$ and $T^2$ together constitute a cyclohexyl, substituted cyclohexyl, cyclohexenyl or substituted cyclohexenyl radical and z is 3.

16. The method of claim 1, wherein $T^1$ and $T^2$ together constitute a cyclohexyl, substituted cyclohexyl, cyclohexenyl or substituted cyclohexenyl radical and z is 3 and A is —CO—.

17. The method of claim 1, wherein $T^1$ and $T^2$ together constitute a cyclohexyl, substituted cyclohexyl, cyclohexenyl or substituted cyclohexenyl radical and z is 3 and A is —CO— and Q is methyl.

18. The method of claim 1, wherein $T^1$ and $T^2$ together constitute a cyclohexyl, substituted cyclohexyl, cyclohexenyl or substituted cyclohexenyl radical and z is 3 and A is —CO— and Q is phenyl or substituted phenyl.

19. The method of claim 1, wherein $T^1$ and $T^2$ together constitute a cyclohexyl, substituted cyclohexyl, cyclohexenyl or substituted cyclohexenyl radical and Q is methyl.

20. The method of claim 1, wherein $T^1$ and $T^2$ together constitute a cyclohexyl radical.

21. The method of claim 1, wherein $T^1$ and $T^2$ together constitute a cyclohexyl radical and Q is methyl.

22. The method of claim 1, wherein $T^1$ and $T^2$ together constitute a cyclohexyl radical and z is 3.

23. The method of claim 1, wherein $T^1$ and $T^2$ together constitute a cyclohexyl radical and z is 3 and Q is methyl.

24. The method of claim 1, wherein the compound is selected from the group consisting of:
- —(S)-3-(2'-hydroxy-1'-methylcyclohexanecarbonyl) amino-caprolactam;
- —(S)-3-(1'-Phenylcyclohexanecarbonyl)amino-caprolactam;
- —(S)-3-(1'-Phenylcyclohexanecarbonyl)amino-tetrahydropyridin-2-one;
- —(S)-3-(cis-4'-tert-Butyl-1'-methyl-1'-cyclohexanecarbonyl)amino-caprolactam;
- —(S)-3-(1'-Methylcyclohexanecarbonyl)amino-tetrahydropyridin-2-one;
- —(S)-3-(1'-Methylcyclohexanecarbonyl)amino-pyrrolidin-2-one;
- —(S)-3-(1'-((tert-Butoxycarbonylamino)cyclopentanecarbonyl)amino-caprolactam;
- —(S)-3-(3'-hydroxy-1'-adamantanecarbonyl)amino-caprolactam;

and sulfonyl analogues thereof;

and pharmaceutically acceptable salts thereof.

25. The method of claim 1, wherein the inflammatory disorder is selected from the group consisting of autoimmune diseases, vascular disorders, viral infection or replication, asthma, osteoporosis, tumor growth, rheumatoid arthritis, organ transplant rejection and/or delayed graft or organ function, a disorder characterised by an elevated TNF-α level, psoriasis, skin wounds, disorders caused by intracellular parasites, allergies, Alzheimer's disease, antigen induced recall response, immune response suppression, multiple sclerosis, ALS, fibrosis, and formation of adhesions.

26. A library consisting of two or more compounds all of which have structures according to the formula (I) of claim 1, which library is useful for screening compounds for novel or improved properties in an assay of anti-inflammatory activity.

27. The method of claim 2, wherein the ring or rings specified by $T^1$ and $T^2$ constrain the bond angles at the alpha-carbon to be essentially tetrahedral (i.e, sp3 hybrid bonds).

28. The method of claim 2, wherein A is —CO—.

29. The method of claim 2, wherein Q is methyl.

30. The method of claim 2, wherein Q is phenyl or substituted phenyl.

31. The method of claim 2, wherein A is —CO— and Q is methyl.

32. The method of claim 2, wherein A is —CO— and Q is phenyl or substituted phenyl.

33. The method of claim 2, wherein z is 2 or 3.

34. The method of claim 2, wherein z is 3.

35. The method of claim 2, wherein z is 3 and A is —CO—.

36. The method of claim 2, wherein z is 3 and A is —CO— and Q is methyl.

37. The method of claim 2, wherein z is 3 and A is —CO— and Q is phenyl or substituted phenyl.

38. The method of claim 2, wherein $T^1$ and $T^2$ together constitute a cyclohexyl, substituted cyclohexyl, cyclohexenyl or substituted cyclohexenyl radical.

39. The method of claim 2, wherein $T^1$ and $T^2$ together constitute a cyclohexyl, substituted cyclohexyl, cyclohexenyl or substituted cyclohexenyl radical and z is 3.

40. The method of claim 2, wherein $T^1$ and $T^2$ together constitute a cyclohexyl, substituted cyclohexyl, cyclohexenyl or substituted cyclohexenyl radical and z is 3 and A is —CO—.

41. The method of claim 2, wherein $T^1$ and $T^2$ together constitute a cyclohexyl, substituted cyclohexyl, cyclohexenyl or substituted cyclohexenyl radical and z is 3 and A is —CO— and Q is methyl.

42. The method of claim 2, wherein $T^1$ and $T^2$ together constitute a cyclohexyl, substituted cyclohexyl, cyclohexenyl or substituted cyclohexenyl radical and z is 3 and A is —CO— and Q is phenyl or substituted phenyl.

43. The method of claim 2, wherein $T^1$ and $T^2$ together constitute a cyclohexyl, substituted cyclohexyl, cyclohexenyl or substituted cyclohexenyl radical and Q is methyl.

44. The method of claim 2, wherein $T^1$ and $T^2$ together constitute a cyclohexyl radical.

45. The method of claim 2, wherein $T^1$ and $T^2$ together constitute a cyclohexyl radical and Q is methyl.

46. The method of claim 2, wherein $T^1$ and $T^2$ together constitute a cyclohexyl radical and z is 3.

47. The method of claim 2, wherein $T^1$ and $T^2$ together constitute a cyclohexyl radical and z is 3 and Q is methyl.

48. The method of claim 2, wherein the inflammatory disorder is selected from the group consisting of autoimmune diseases, vascular disorders, viral infection or replication, asthma, osteoporosis, tumor growth, rheumatoid arthritis, organ transplant rejection and/or delayed graft or organ function, a disorder characterised by an elevated TNF-α level, psoriasis, skin wounds, disorders caused by intracellular parasites, allergies, Alzheimer's disease, antigen induced recall response, immune response suppression, multiple sclerosis, ALS, fibrosis, and formation of adhesions.

49. A library consisting of two or more compounds all of which have structures according to the formula (I') of claim 2, which library is useful for screening compounds for novel or improved properties in an assay of anti-inflammatory activity.

\* \* \* \* \*